United States Patent [19]

Tabuchi

[11] Patent Number: 5,355,067
[45] Date of Patent: Oct. 11, 1994

[54] APPARATUS FOR CONTROLLING A STEPPING MOTOR USED FOR DRIVING A CHEMICAL PUMP AND METHOD OF CONTROLLING A STEPPING MOTOR USED FOR DRIVING A CHEMICAL PUMP

[75] Inventor: Masazumi Tabuchi, Osaka, Japan
[73] Assignee: Sharp Kabushiki Kaisha, Osaka, Japan
[21] Appl. No.: 771,980
[22] Filed: Oct. 8, 1991
[30] Foreign Application Priority Data Oct. 19, 1990 [JP] Japan .................. 2-282565

[51] Int. Cl.$^5$ .......................................... H02P 7/06
[52] U.S. Cl. ........................... 318/696; 318/799
[58] Field of Search .............. 318/696, 798–800

[56] References Cited

U.S. PATENT DOCUMENTS

| 3,701,345 | 10/1972 | Heilman et al. |
| 3,855,515 | 12/1974 | Hutchins, Jr. |
| 4,330,739 | 5/1982 | Chiang ................... 318/696 |
| 4,444,546 | 4/1984 | Pazemenas . |
| 4,817,887 | 4/1989 | Harigaya et al. ............ 318/7 |
| 4,868,477 | 9/1989 | Anderson et al. ......... 318/696 |
| 4,882,530 | 11/1989 | Kabune . |
| 4,888,542 | 12/1989 | Muranaka ............. 318/696 |
| 4,943,760 | 7/1990 | Bryne et al. ............. 318/701 |
| 4,954,764 | 9/1990 | Kim ................... 318/798 |
| 4,961,038 | 10/1990 | MacMinn .............. 318/696 |
| 5,068,586 | 11/1991 | Kawahara et al. ........ 318/696 |

FOREIGN PATENT DOCUMENTS

| 0127346 | 12/1984 | European Pat. Off. . |
| 0251776 | 1/1988 | European Pat. Off. . |
| 0394941 | 10/1990 | European Pat. Off. . |
| 0414436 | 2/1991 | European Pat. Off. . |
| 59-123196 | 7/1984 | Japan . |
| 1-80684 | 5/1989 | Japan . |

Primary Examiner—William M. Shoop, Jr.
Assistant Examiner—Brian Sircus
Attorney, Agent, or Firm—Nixon & Vanderhye

[57] ABSTRACT

An apparatus for controlling a stepping motor (11) used for driving a chemical pump includes a random access memory (16) for storing a minimum current value required for driving the chemical pump at each of divisional intervals of one cycle of the chemical pump, two photo interrupters (13, 14) for sensing an angular location of the stepping motor (11) corresponding to each of the intervals of the chemical pump, and a central processing unit (17) connected to the two photo interrupters (13, 14) for controlling the stepping motor (11) in accordance with the angular location of the stepping motor (11) sensed by the two photo interrupters (13, 14), the central processing unit (17) being so arranged that it uses the minimum current value required for driving the chemical pump at an angular location following the angular location sensed by the two photo interrupters (13, 14).

7 Claims, 5 Drawing Sheets

APPARATUS FOR CONTROLLING A STEPPING MOTOR USED FOR DRIVING A CHEMICAL PUMP AND METHOD OF CONTROLLING A STEPPING MOTOR USED FOR DRIVING A CHEMICAL PUMP

BACKGROUND OF THE INVENTION

1. Field of the Invention

The present invention relates to a control apparatus for a stepping motor used for driving a chemical pump, more particularly, a control apparatus which is capable of controlling a chemical pump so that a driving torque of the chemical pump changes in one cycle.

2. Description of the Related Art

A chemical pump for injecting a chemical into a human body is required to drive a chemical injecting pump so that the chemical is allowed to be injected into a human body at a constant flow.

The inventors of the present invention know that a chemical pump normally utilizes a stepping motor and there has been proposed a control apparatus for controlling a stepping motor used for driving a chemical pump.

Referring to FIG. 1, a known control apparatus for controlling the stepping motor used as the chemical pump will be described in the following part.

The known control apparatus for controlling the stepping motor used for driving a chemical pump is so arranged that the stepping motor 21 is controlled in a manner that the chemical pump (not shown) may be driven in a step-wise manner.

A rotation of the stepping motor 21 is sensed by a photo interrupter 22 which is connected with a central processing unit (CPU) 23. The CPU 23 determines whether or not the stepping motor 21 loses its synchronism in accordance with a signal sensed by the photo interrupter 22. In addition, the CPU 23 controls the driving current for the stepping motor 21.

FIG. 2 is a plot showing a characteristic of the stepping motor 21. The plot indicates that the torque generated by the stepping motor 21 is proportional to the driving current (motor current).

That is, as the driving current becomes larger, the power consumption becomes larger. Hence, considering the torque and the power consumption, it is necessary to utilize the CPU 23 in a manner that the stepping motor 21 is operated according to the steps of the processes shown in FIG. 3.

As shown in FIG. 3, the stepping motor 21 is started with a relatively high driving current (step T1). Then, the number in a counter n is reset to "0" (step T2). The number in the counter n indicates how often the driving current is changed. At a next step, it is checked whether or not the stepping motor 21 loses its synchronism depending on the signal sent from the photo interrupter 21 (step T3).

In a case that a result of the above step T3 is yes, then, the driving current is a bit increased (step T4) and it is determined whether or not the increased current is larger than a predetermined value (step T5). In a case that a result of the above step T5 is no, then the process returns to the step On the contrary, in a case that a result of the above step T5 is yes, then the error processing is executed.

At the step T3, in a case that the stepping motor 21 does not lose its synchronism, then the number of the counter n is incremented (step T6) and it is determined whether or not the value of the number of the counter n is equal to or larger than a predetermined value N (step T7). Depending on the determined result at the step T7, in a case that the value of the number of the counter n is equal to or larger than a predetermined value N, then the operation of the stepping motor 21 is continued. On the other hand, in a case that the value of the number of the counter n is less than the predetermined value N, then the motor current is bit decreased (step T8), and the process is returned to the above-mentioned step T3 for further operation.

Referring to FIG. 4, the known control apparatus for the stepping motor actuates the stepping motor 21 with a relatively large driving current. Then, the driving current is gradually reduced N times. It results in keeping the driving current of the stepping motor 21 substantially constant. In a case that the stepping motor 21 loses its synchronism, the driving current is a bit increased so as to amend the loss of synchronism of the stepping motor 21.

The known control apparatus for the stepping motor used for driving the chemical pump, however, has a shortcoming in that the loss of the driving current is large, because the stepping motor 21 is driven with such a substantially constant driving current so as to keep the driving torque at maximum in order to prevent the loss of synchronism of the stepping motor.

SUMMARY OF THE INVENTION

It is therefore a first object of the present invention to provide an apparatus for controlling a stepping motor used for driving a chemical pump and capable of changing a driving current of the stepping motor in accordance with a change of driving torque in a case that driving torque of the chemical pump is fluctuated within one cycle.

It is a second object of the present invention to provide a method of controlling a stepping motor used for driving a chemical pump so that a driving current of the stepping motor is changed in accordance with a change of a driving torque in a case that driving torque of the chemical pump is fluctuated within one cycle.

The first object of the present invention can be achieved by an apparatus for controlling a stepping motor used for driving a chemical pump includes a unit for storing a minimum current value required for driving the chemical pump at each of divisional intervals of one cycle of the chemical pump, a unit for sensing an angular location of the stepping motor corresponding to each of the intervals of the chemical pump, and a unit connected to the sensing unit for controlling the stepping motor in accordance with the angular location of the stepping motor sensed by the sensing unit, the controlling unit being so arranged that it uses the minimum current value required for driving the chemical pump at an angular location following the angular location sensed by the sensing unit.

Preferably, the storing unit is a random access memory.

More preferably, the sensing unit is two photo interrupters, one of the photo interrupters being capable of sensing a rotation of the stepping motor and the other one of the photo interrupters being capable of sensing a driven portion of the stepping motor.

Further preferably, the control unit is a central processing unit.

The divisional intervals are preferably composed of five areas, each of the five areas having a rotating angle of 72°.

The apparatus further includes a read-only memory for storing a program for executing a control of the stepping motor by the controlling unit.

In operation, the storage unit stores a minimum current value for driving the chemical pump at each of the divisional intervals of one cycle. The sensing unit serves to sense an angular location of the stepping motor corresponding to each cycle of the chemical pump. The control unit serves to control the stepping motor with a minimum current value required for driving the chemical pump at the angular location following the location sensed by the sensing unit. The driving current of the stepping motor may change depending on the driving torque of the chemical pump being fluctuated in one cycle. It results in reducing the driving current at any proper time for lowering the power consumption, thereby allowing the present control apparatus to efficiently control the stepping motor and drive the chemical pump.

The second object of the present invention can be achieved by a method of controlling a stepping motor used for driving a chemical pump includes a step of setting a plurality of initial values of a driving current with respect to each of divisional intervals of one cycle of the chemical pump, a step of setting a number of a count $n(r)$ for each of the divisional intervals to be "0", the number of the count $n(r)$ indicating how often the driving current has been reduced and wherein r is an integer from 1 to 5, a step of reading a current angular location of the stepping motor through an effect of a photo interrupter so as to set an area number r, a step of setting an initial value $I(r)$ for a driving current corresponding to the area number r so as to set an actual current I, a step of detecting a rotation of the stepping motor by the photo interrupter so as to check whether the stepping motor loses a synchronism thereof, a step of increasing a bit of the driving current $I(r)$ in a case that a result of the above check indicates that the stepping motor loses its synchronism so as to set as increased driving current $I'(r)$, a step of incrementing the number of the count $n(r)$ by one such that the $n(r)=n(r)+1$ in a case that the stepping motor does not lose a synchronism thereof, a step of determining whether the value of the count $n(r)$ is equal to a predetermined value N, and a step of reducing the driving current $I(r)$ of the stepping motor in a case that the value of the count $n(r)$ is less than the predetermined value N so as to set a reduced driving current $I''(r)$.

Further objects and advantages of the present invention will be apparent from the following description of the preferred embodiment of the invention as illustrated in the accompanying drawings.

DESCRIPTION OF THE PREFERRED EMBODIMENT

Referring to the accompanying drawings, an embodiment of an apparatus for controlling a stepping motor used for driving a chemical pump according to the present invention will be described in details in the following sections.

Figure 1:
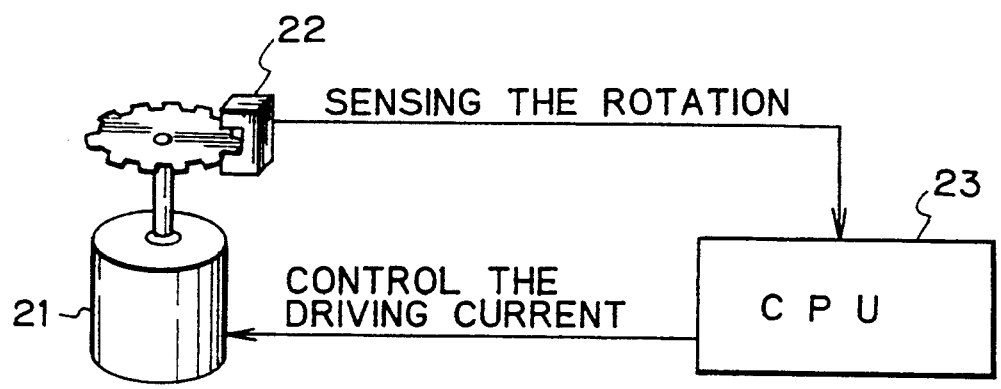
FIG. 1 is a schematic view showing arrangement of a control apparatus for a stepping motor used for driving a chemical pump according to a related art of the invention.
Figure 2:
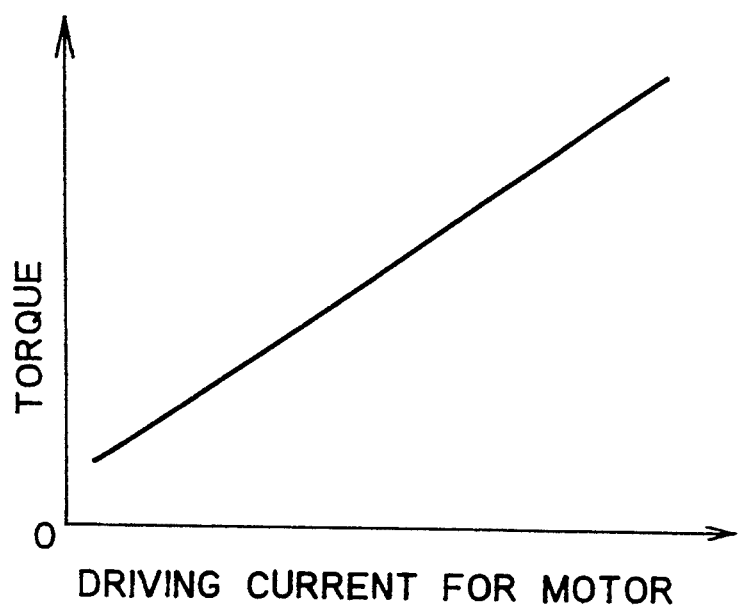
FIG. 2 is a plot showing a characteristic of the stepping motor used for a chemical pump shown in FIG. 1.
Figure 3:
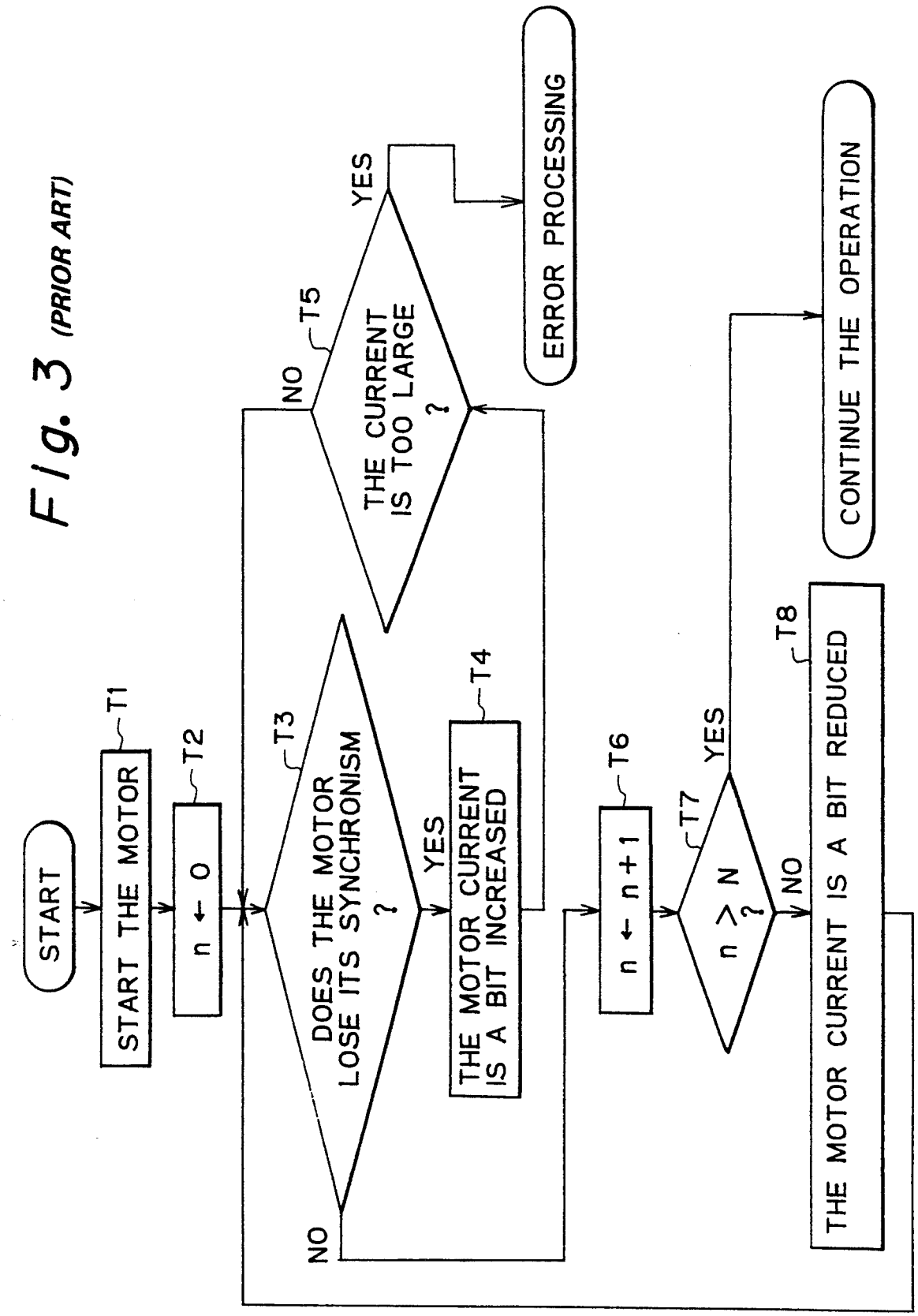
FIG. 3 is a flowchart showing operation of the control apparatus shown in FIG. 1.
Figure 4:
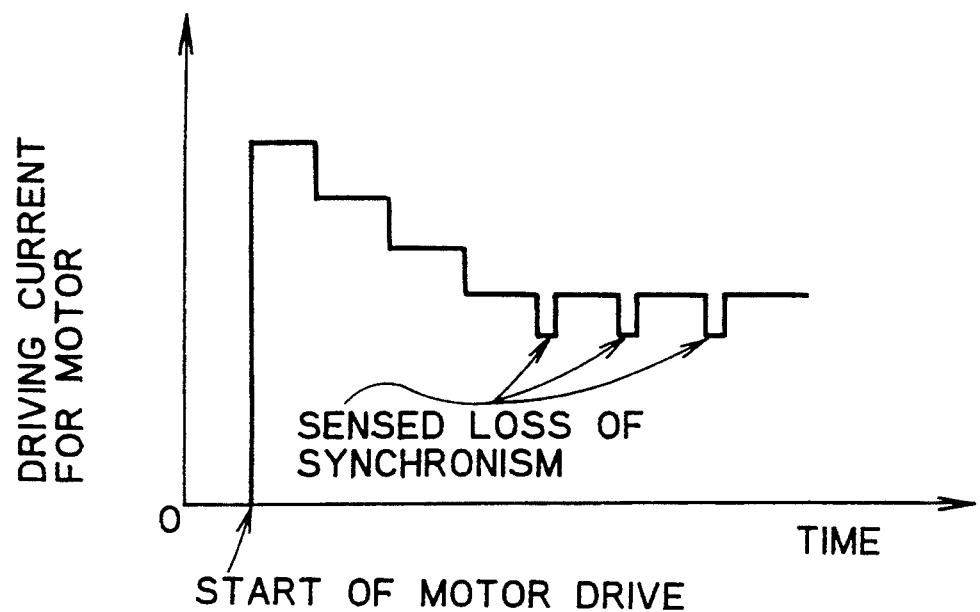
FIG. 4 is an explanatory plot showing the driving current arranged by the control apparatus shown in FIG. 1.
Figure 5:
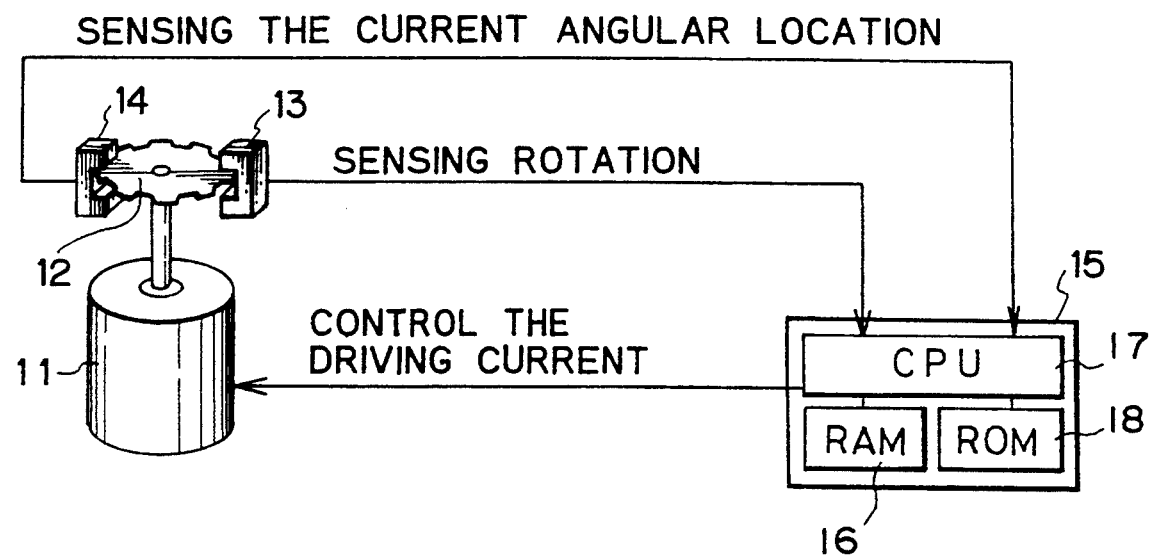
FIG. 5 is a schematic view showing a control apparatus for a stepping motor used for driving a chemical pump according to an embodiment of the invention.

FIG. 5 is a schematic view showing an arrangement of an embodiment of the control apparatus according to the present invention.

As shown in FIG. 5, the control apparatus includes a stepping motor 11, a driving portion 12 of the stepping motor 11, two photo interrupters 13, 14 and a control unit 15. Two photo interrupters 13, 14 are located adjacent to the driven portion 12 of the stepping motor 11 (meaning that part of a chemical pump).

A rotation of the stepping motor 11 is allowed to be sensed from the driven portion 12 by the photo interrupter 13.

The angular location of the stepping motor 11 can be obtained by sensing the location of the driven portion 12 with the photo interrupter 14.

According to this embodiment, the stepping motor 11 is arranged to rotate once for one operating period of the chemical pump in the following parts for better understanding of the operation of the apparatus of the present invention.

That is, one rotation of the stepping motor 11 is equivalent to one operating period of the chemical pump. In other words, the operation of the chemical pump at each one cycle is allowed to be sensed by the rotation of the stepping motor 11.

Figure 6:
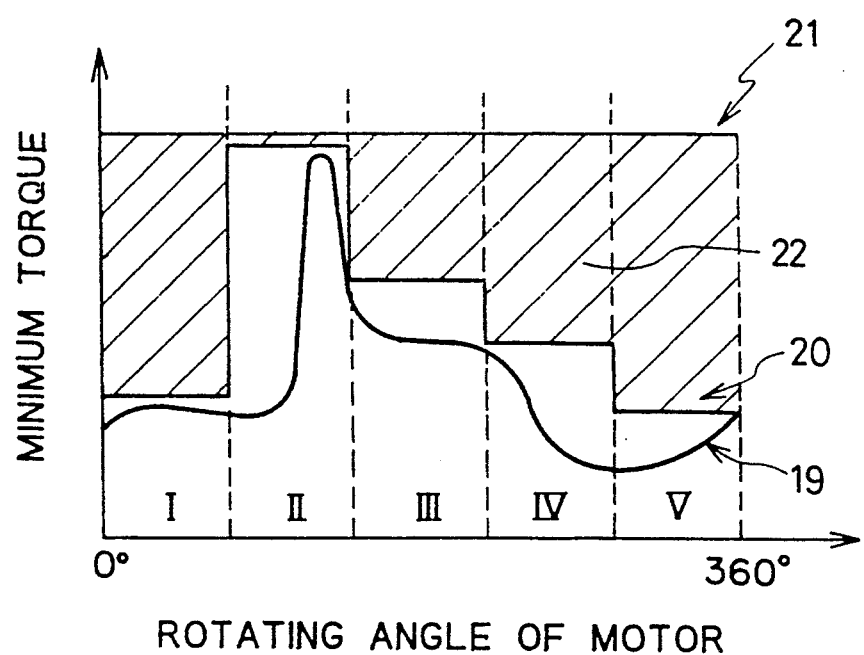
FIG. 6 is an explanatory plot showing driving current arranged by the control apparatus shown in FIG. 5.

Depending on the fluctuation of the driving torque of the chemical pump in one cycle, one rotation of the stepping motor 11 is divided into five areas I to V as shown in FIG. 6.

The control unit 15 includes a random access memory 16 for storing an initial current value required for driving the stepping motor 11 at each of the areas I to V without fail. The control unit 15 also includes a central processing unit 17 for controlling the driving current so as to prevent the loss of synchronism of the stepping motor 11. The control of the driving current is executed on the basis of the initial current value required for driving the stepping motor 11 at the area corresponding to the rotating location sensed by the photo interrupter 13.

The control unit 15 further includes a read-only memory 18 and the other active elements (not shown). The read-only memory 18 stores a program which is executed in accordance with the steps of the processes shown in FIG. 7.

Figure 7:
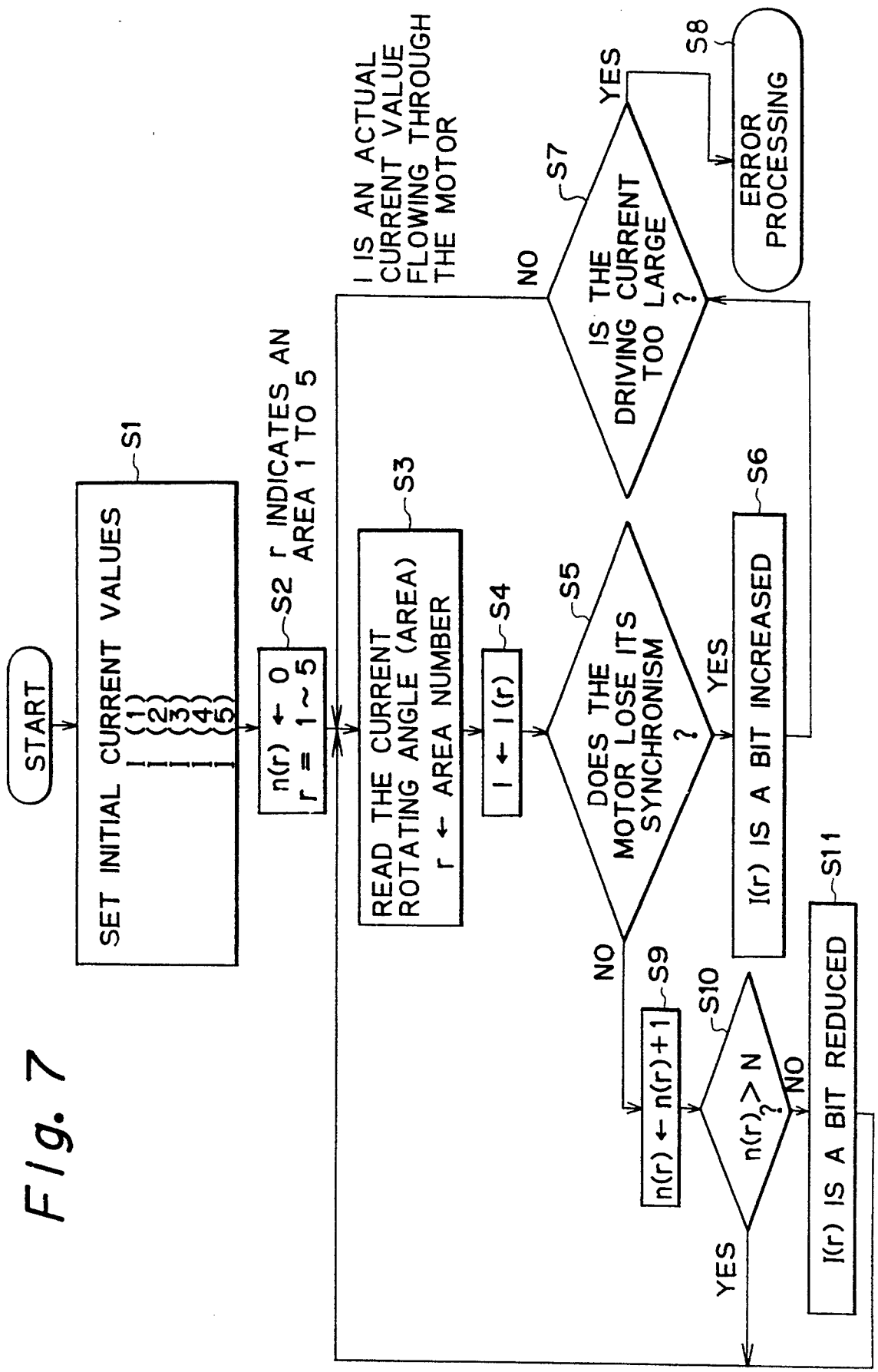
FIG. 7 is a flowchart showing operation of the control apparatus shown in FIG. 5.

Referring to FIGS. 6 and 7, the operation of the control apparatus for the stepping motor, featuring the operation of the control unit 15 will be described.

Initial values $I(1)$, $I(2)$, $I(3)$, $I(4)$ and $I(5)$ of the driving current are set for the areas I to V (step S1). A number of a count $n(r)$ for each area is set to "0". The number of the count $n(r)$ indicates how often the driving current is changed. Herein, r is assumed to have 1 to 5 (step S2). For r=1 for the area I, r=2 for the area II, r=3 for the area III, r=4 for the area IV and r=5 for the area V, respectively, are set.

A current angular location of the stepping motor 11, that is, the current driven portion 12 is read through the effect of the photo interrupter 14 and is set as an area number r (step S3). An initial value I(r) for a driving current corresponding to an area number r is set as an actual driving current I (step S4).

Then, the rotation of the stepping motor 11 is sensed the photo interrupter 13 so as to check whether or not the stepping motor 11 loses its synchronism (step S5).

In a case that a result of the above check at the step indicates that the stepping motor 11 loses its synchronism, the operation goes to a step S6 at which the driving current I'(r) is a bit increased and is set as the driving current I'(r).

In a case that the increased driving current I'(r) is not larger than a predetermined value, the operation returns to the step S3 (step S7). On the other hand, in a case that the increased driving current I(r) is larger than the predetermined value, the error processing is executed (step S8).

In a case that it is checked that the stepping motor 11 does not lose its synchronism at the step S5, then the number of the count n(r) is incremented by one such that n(r)=n(r)+1 is established (step S9). Then, it is determined whether or not the value of the count n(r) is equal to or larger than a predetermined value N (step S10).

In a case that the value of the count n(r) is less than the predetermined value N at the step S10, then the driving current I(r) of the stepping motor 11 is a bit reduced and is set as the driving current I(r), and the operation returns to the step S3 (step S11).

In a case that the value of the number of the count n(r) becomes larger than the predetermined value N, the operation directly returns from the step S10 to the step S3, because it is not necessary to reduce the driving current I(r).

In succession, at the step S3, the area of the driven portion 12 following the proceeding area is read by the photo interrupter 14. Then the foregoing operation is repeated for controlling the stepping motor 11.

According to the present embodiment, as shown in FIG. 6, the torque 19 required for the operation of the chemical pump becomes maximum in the area II where the rotating location of the stepping motor 11 ranges from 72° to 144°. The torque 19 required therefore is reduced in the sequence of the areas III, IV and V. The area III has the rotating location of the stepping motor 11 ranging from 144° to 216°, the area IV has the rotating location of the stepping motor 11 ranging from 16° to 288°, and the area V has the rotating location of the stepping motor 11 ranging from 288° to 360°.

FIG. 6 is a plot showing a characteristic of the driving current 20 arranged by the control apparatus for the stepping motor according to the present embodiment. The driving current 20 has a specific value to each of the areas I to V.

The driving current 20 is controlled so that it becomes minimum at each of the areas I to V. The minimum value is represented as an initial average value changed in a step-wise manner.

A driving current 21 represents a driving current arranged by the above-mentioned known control apparatus for a comparison, and the driving current 21 is equal to a maximum value in the area II having the rotating location ranging from 72° to 144° and is kept constant. As mentioned above, in the area II, the maximum torque is required for the operation of the chemical pump.

The portion shown by oblique lines of FIG. 6 indicates the difference between the driving current 20 arranged by the control apparatus of this embodiment and the driving current 21 arranged by the above-mentioned known control apparatus. It will be easily understood from FIG. 6 that the driving current 20 is smaller than the driving current 21.

This portion is referred to as a driving current difference 22. As the driving current difference 22 becomes larger, the driving current 20 is reduced as compared with the driving current 21 of the above-mentioned known control apparatus, resulting in greatly reducing the power consumption, thereby enhancing the efficiency of the stepping motor.

Many widely different embodiments of the present invention may be constructed without departing from the spirit and scope of the present invention. It should be understood that the present invention is not limited to the specific embodiments described in the specification, except as defined in the appended claims.

What is claimed is:

1. A method of controlling a stepping motor used for driving a chemical pump, said method comprising the steps of:

setting a plurality of initial values of a driving current to obtain a plurality of torque values in each of a respective plurality of divisional intervals of one cycle of said chemical pump;

initializing a count variable n(r) to 0 for each of said divisional intervals, said number of said count n(r) indicating how often said driving current has been reduced for an interval r, and wherein r is an integer from 1 to 5;

reading a current angular location of said stepping motor using a photo interrupter so as to set said number r;

setting an initial value I(r) for a driving current corresponding to said set number r so as to set an actual current I;

detecting a rotation of said stepping motor by said photo interrupter so as to determine whether said stepping motor loses synchronism;

incrementing said driving current I(r) when it is determined that the stepping motor loses synchronism so as to set an increased driving current, incrementing said number of said count n(r) by one so that n(r)=n(r)+1 when said stepping motor does not lose synchronism;

determining whether said value of said count n(r) is equal to a predetermined value N; and reducing said driving current I(r) of said stepping motor when said value of said count n(r) is less than said predetermined value N so as to set a reduced driving current.

2. A method as in claim 1 wherein the steps following said initializing step are repeated for each of said divisional intervals.

3. A method as in claim 2 wherein said steps are repeated for each cycle of said chemical pump.

4. A method as in claim 1 wherein each of said divisional intervals includes a rotational angle of 72°.

5. An apparatus for controlling a stepping motor used for driving a chemical pump, comprising:

means for setting a plurality of initial values for a driving current to obtain a plurality of torque values in each of a respective plurality of divisional intervals of one cycle of said chemical pump;

means for initializing a count variable $n(r)$ to 0 for each of said divisional intervals, said number of said count $n(r)$ indicating how often said driving current has been reduced for an interval r, and wherein r is an integer from 1 to 5;

means for reading a current angular location of said stepping motor using a photo interrupter so as to set said number r;

means for setting an initial value $I(r)$ for a driving current corresponding to said set number r so as to set an actual current I;

means for detecting a rotation of said stepping motor by said photo interrupter so as to determine whether said stepping motor lose synchronism;

means for incrementing said driving current $I(r)$ when it is determined that the stepping motor loses synchronism so as to set an increased driving current, incrementing said number of said count $n(r)$ by one so that $n(r)=n(r)+1$ when said stepping motor does not lose synchronism;

means for determining whether said value of said count $n(r)$ is equal to a predetermined values N; and means for reducing said driving current $I(r)$ of said stepping motor when said value of said count $n(r)$ is less than said predetermined value N so as to set a reduced driving current.

6. An apparatus as claimed in claim 5, wherein the functions of the means recited subsequent to said initializing means are arranged to be executed repeatedly for each of said divisional intervals.

7. An apparatus as claimed in claim 6, wherein the functions of the means recited subsequent to said initializing means are arranged to be executed repeatedly for each cycle of said chemical pump.

* * * * *